(12) United States Patent
Scheib

(10) Patent No.: US 8,401,631 B2
(45) Date of Patent: Mar. 19, 2013

(54) METHOD AND SYSTEM FOR MONITORING PHYSIOLOGICAL CONDITIONS

(76) Inventor: Christopher Scheib, Nicholasville, KY (US)

( * ) Notice: Subject to any disclaimer, the term of this patent is extended or adjusted under 35 U.S.C. 154(b) by 395 days.

(21) Appl. No.: 12/925,296

(22) Filed: Oct. 18, 2010

(65) Prior Publication Data

US 2011/0125047 A1 May 26, 2011

Related U.S. Application Data

(63) Continuation-in-part of application No. 12/589,047, filed on Oct. 16, 2009, now Pat. No. 8,352,021, which is a continuation-in-part of application No. 12/082,842, filed on Apr. 15, 2008, now Pat. No. 7,720,531.

(60) Provisional application No. 61/279,110, filed on Oct. 16, 2009.

(51) Int. Cl.
*A61B 5/04* (2006.01)

(52) U.S. Cl. .................................. 600/544; 600/545

(58) Field of Classification Search ............. 600/300, 600/544–545, 26; 340/575–576
See application file for complete search history.

(56) References Cited

U.S. PATENT DOCUMENTS 5,813,993 A * 9/1998 Kaplan et al. ............... 600/544

* cited by examiner

*Primary Examiner* — Patricia Mallari
*Assistant Examiner* — Michael D'Angelo
(74) *Attorney, Agent, or Firm* — Stockwell & Smedley, PSC

(57) ABSTRACT

A method for providing an indication of a state of awareness for a patient, includes the steps of arranging data of an EEG and EMG power spectrogram to provide power versus frequency in a log-log arrangement; calculating a first best-fit line for a lower frequency region of the EEG power spectrogram; calculating at least a second best-fit line for a higher frequency region of the EEG power spectrogram. The display of these lines is augmented by displaying a template that identifies different regions on the display that help confirm the state of the patient. Secondly, the time domain EEG signals can be filtered and displayed such that different frequency bands can be simultaneously displayed or a single frequency band can be displayed according to different time scales.

20 Claims, 6 Drawing Sheets

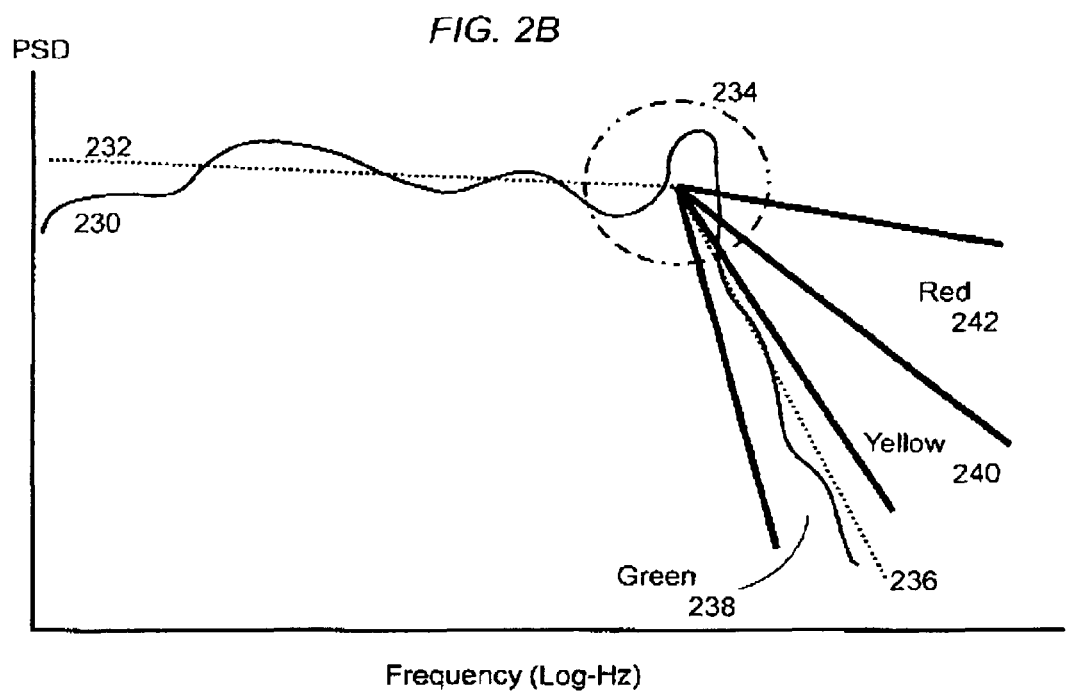
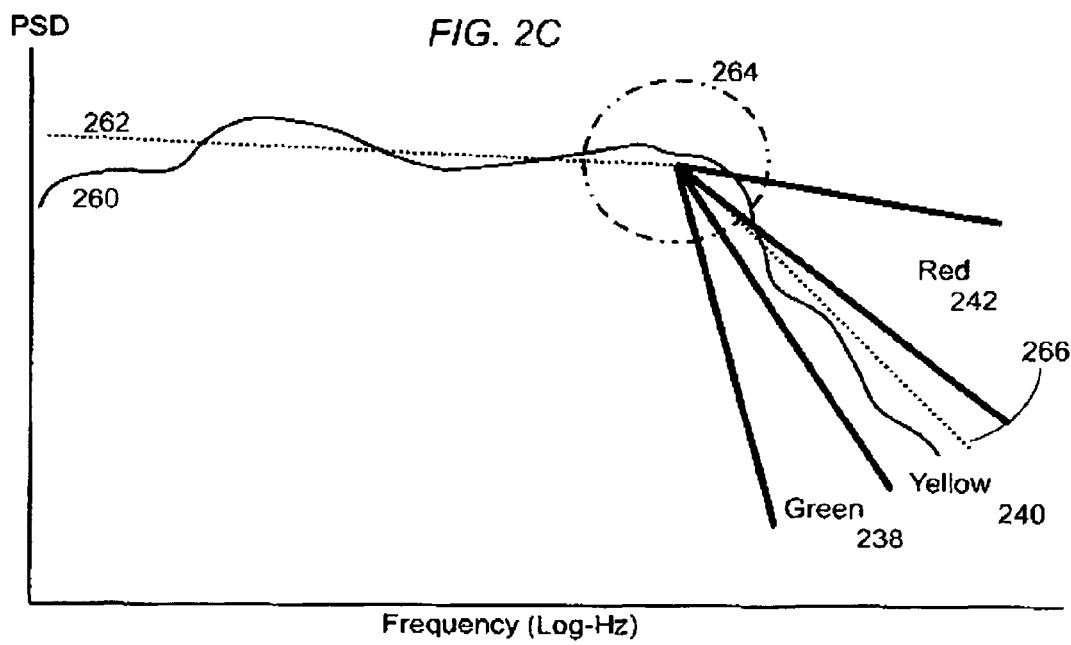

METHOD AND SYSTEM FOR MONITORING PHYSIOLOGICAL CONDITIONS

RELATED APPLICATIONS

The present invention is a continuation-in-part of the previously filed U.S. patent application Ser. No. 12/589,047 filed Oct. 16, 2009 which is a continuation-in-part of the previously filed U.S. patent application Ser. No. 12/082,842 filed Apr. 15, 2008 (now U.S. Pat. No. 7,720,531), the disclosures of which is incorporated herein in their entirety. Priority is claimed, as well, to the provisional patent application Ser. No. 61/279,110 filed Oct. 16, 2009, the disclosure of which is incorporated by reference in its entirety.

BACKGROUND

Field

The present invention relates generally to monitoring brain function during different states of consciousness such as general anesthesia, coma or natural sleep and, more particularly, to using electroencephalogram (EEG) data and other physiological data to evaluate brain function.

The definition of the term "anesthesia" is—a lack of aesthesia—or lack of sensation. For surgical purposes this is generally achieved in two main ways: 1) infiltration of a peripheral or more central nerve bundle with a local anesthesia, which prevents the nerve impulse being processed by the central nervous system and, thus, sensation (of pain or otherwise is not perceived by the individual who remains conscious and aware; and 2) general anesthesia which requires a loss of consciousness in order for the sensation not to be perceived by the individual. To date no systems of monitoring brain function has produced a reference point beyond which one can absolutely state that there exists a complete lack of consciousness at an anesthetic dosage level low enough to be of practical value. Present systems merely produce a measure of probability of loss of consciousness when the anesthetic dosage level is at the low end of the practical range.

The "depth of anesthesia" generally describes the extent to which consciousness is lost following administration of an anesthetic agent. As the magnitude of anesthetization, or depth of anesthesia, increases, an anesthetized patient typically fails to successively respond to spoken commands, loses the eyelid reflex, loses other reflexes, undergoes depression of vital signs, and the like. Once consciousness is lost there is a progression of effects on brain function as higher concentrations or dose of anesthetic agent are administered.

For clinical use, it is desirable to simplify the results of EEG signal analysis of the foregoing, and other types, into a workable parameter that can be used by an anesthesiologist in a clinical setting when attending the patient. Prior techniques have included showing the EEG signal in a relatively unprocessed form or showing a number (or letter) without any other underlying data supporting that number. Neither solution is helpful in a clinical setting; especially, in the case of the "number" indicator, when the number is at best a probability that the patient is not aware or conscious. Ideally, what is desired is a simple indicator that accurately indicates the patient's lack of awareness and how far below the transition to awareness the patient is. The indicator should also account for phenomena that vary by patient such as, for example, the less pronounced a peak of older patients and the possible occurrence of a burst suppression event. Thus, there remains a need for such an indicator that reliably and quickly indicates awareness during general anesthesia and the depth of anesthesia.

SUMMARY

Embodiments of the present invention relate to a system and method for determining from EEG signals the lack of awareness and the depth of anesthesia of a patient to whom an anesthetic agent is being administered. In particular, a log-log representation of the EEG power spectrum is converted to multiple, best-fit intersecting lines so that the intersection point and the absolute and relative slopes can be analyzed to determine a state of anesthesia of a patient. This system and method may also be used in an analysis of the brain function of a sleeping individual to distinguish between awareness, REM sleep, and the various levels of non-REM sleep. It may also be used to investigate the effect of various experimental pharmaceuticals on brain function.

Other embodiments of the present invention relate to another system and method for determining from EEG signals the lack of awareness and the depth of anesthesia of a patient to whom an anesthetic agent is being administered. In particular, the EEG signal is displayed as multiple filtered signals that together allow a visual determination regarding the state of the patient. In some instances the multiple filtered signals may be superimposed and in other instances they may be displayed separately. This system and method may also be used in an analysis of the brain function of a sleeping individual to distinguish between awareness, REM sleep, and the various levels of non-REM sleep. It may also be used to investigate the effect of various experimental pharmaceuticals on brain function.

It is understood that other embodiments of the present invention will become readily apparent to those skilled in the art from the following detailed description, wherein it is shown and described only various embodiments of the invention by way of illustration. As will be realized, the invention is capable of other and different embodiments and its several details are capable of modification in various other respects, all without departing from the spirit and scope of the present invention. Accordingly, the drawings and detailed description are to be regarded as illustrative in nature and not as restrictive.

BRIEF DESCRIPTION OF THE DRAWINGS

Various aspects of a system and method for anesthesia monitoring are illustrated by way of example, and not by way of limitation, in the accompanying drawings, wherein:

FIGS. 2B and 2C illustrate a display of the log-log EEG signal in accordance with the principles of the present invention.

DETAILED DESCRIPTION OF THE PREFERRED EMBODIMENTS

The detailed description set forth below in connection with the appended drawings is intended as a description of various embodiments of the invention and is not intended to represent the only embodiments in which the invention may be practiced. The detailed description includes specific details for the purpose of providing a thorough understanding of the invention. However, it will be apparent to those skilled in the art that the invention may be practiced without these specific details. In some instances, well known structures and components are shown in block diagram form in order to avoid obscuring the concepts of the invention.

Figure 1:
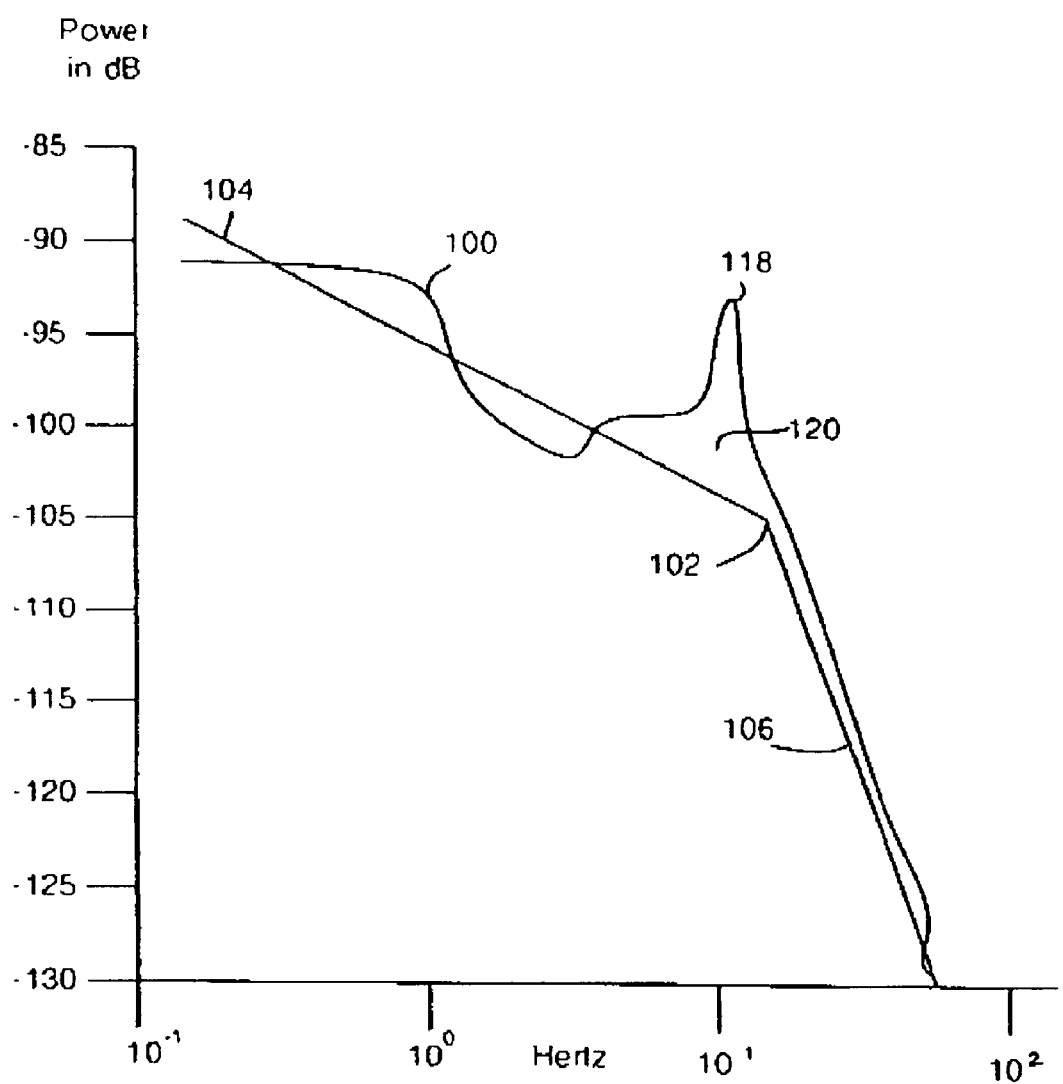
FIG. 1 shows an exemplary log-log EEG power spectrogram in accordance with the principles of the present invention.

In the above-incorporated patent applications the frequency range of contemplated signals extended to about 40 Hz. FIG. 1 shows an exemplary log-log EEG power spectrogram in accordance with the principles of the referenced, incorporated patent application. The spectrogram 100 is that of a patient that is deeply under anesthesia. In other words, the patient has crossed the transition point into a lack of awareness and is relatively far from returning to that transition point. As shown, the power of frequencies above about 12 or 15 Hz significantly drops while the power at the lower frequencies is much higher. In accordance with providing the information in a log-log format, the spectrogram 100 can be transformed into the best-fit lines 104, 106. Regardless of the point of reference from which you measure, the respective slopes of the low frequency line 104 and the high frequency line 106 are vastly different. The intersection point 102 is at about 15 Hz. As noted, this display allows for simple analysis of the anesthetic state, or more generally, the brain function, of a patient.

Additional useful data can be extracted from the graph depicted in FIG. 1. In this graph, an alpha peak 118 is present that would typically be considered an outlier when calculating the best fit line 104. Other peaks may occur in the EEG signal 400 and may be useful as well. One beneficial analysis of such peaks is to use the best fit line 104 as a baseline and subtract it from the signal 100. For the alpha peak 118, for example, the area 120 above the baseline represents information about the alpha peak. For example, its amplitude, its spread, and the center frequency can all be determined by analyzing the area 120. Regression analysis of these parameters revealed that there is a correlation between the alpha peak frequency and concentration of the anesthetic agent. Thus, because the alpha peak generally shifts with concentration of anesthesia (decreasing frequency as concentration increases), the changes in the alpha peak can be used as additional information or confirmation when making a determination about the state of awareness of the patient. In some tests, surgical stimulation (e.g., retracting an inflamed nerve root) also resulted in changes of the alpha peak size and location such as reducing the amplitude of the alpha peak and/or shifting it to a higher or lower frequency. These additional factors may be useful when determining the state of awareness of the patient.

However, additional investigation has established that extending the frequency range to about 130 Hz provides beneficial data and analysis as well. Going from 40 Hz to 130 Hz goes beyond what is traditionally thought of as EEG into the EMG range. Similarly, as before, the EEG (and now EMG) data is plotted in a log-log representation. This representation and extended frequency range allows more than two best-fit lines to be calculated. For example, the raw data can be modeled by 3, 4 or even more best-fit lines. Once these lines are calculated, analysis of the lines can occur. Within this patent application, the terms EEG and EMG are used for convenience to refer to sensing and collecting physiological responses in the frequency ranges from about 0 Hz to about 130 Hz. Use of these terms is not intended to limit the scope of the present invention to only EEG or EMG machines or techniques but, instead, is intended to encompass sensing of the electrical physiological responses produced by a person within the specified frequency range.

The differences in the heights and slopes of each line, the frequency and amplitude of the intersection points, and the angles formed at the intersections all provide useful data in evaluating brain function.

In addition, the presence and location of various peaks in the log-log data are useful as well. The frequency at which the alpha peak and the delta peak occur, for example, provide useful information for evaluating brain function. When used in conjunction with the best-fit line data, the peak locations provide further certainty that the analysis of brain function is accurate. The area under the peak and a corresponding best-fit line is useful as well. The more the peak spreads or the higher the peak is, generally the more area that will be under the peak which is useful information for evaluating brain function.

In one particular example, there is a correlation between the alpha peak frequency and concentration of the anesthetic agent. Thus, data about the alpha peak (e.g., frequency, height, area, etc.) are indicators of brain function in the presence of an anesthetic agent.

Figure 2A:
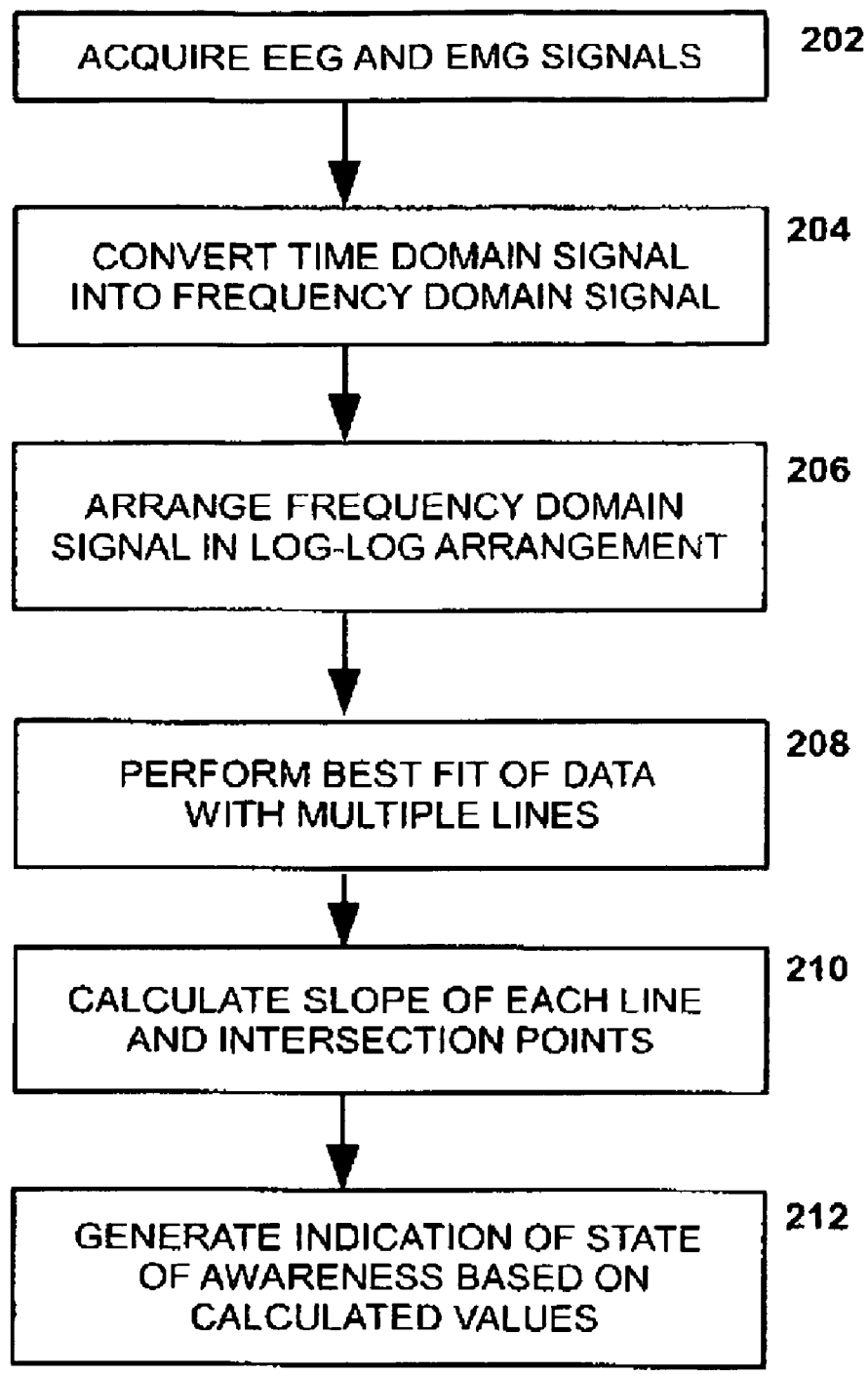
FIG. 2A shows a flowchart of an exemplary algorithm for analyzing EEG spectrograms in accordance with the principles of the present invention.

The flowchart of FIG. 2A depicts an exemplary algorithm for analyzing EEG and EMG spectrograms in accordance with the principles of the present invention. In step 202, the raw EEG signal and EMG signal is captured as is known in the art. For example, signals in the range of approximately 0 to 128 Hz are captured; however, it is contemplated that even higher frequencies may be captured and analyzed as well. Present techniques and devices as well as future-designed EEG and EMG devices may be utilized to acquire the raw signals. Also, as well known in the art, the raw signals may be filtered and processed to reduce noise and to remove artifacts that are known to be introduced into the signals. The raw signal is a time-domain series of samples that are sampled or converted to digital signals which can be then processed by computer platforms or specialized digital signal processors.

Once the digital signals are generated, the time-domain signal can be transformed into a frequency-domain signal in step 204. While there are a number of techniques for converting between the time domain and the frequency domain, a common technique involves the fast Fourier transform method. A number of computationally efficient algorithms for performing fast Fourier transforms beneficially result in a technique that can occur in almost real time with even limited computational power. As one of ordinary skill will recognize, there are a number of parameters that can be selected to control how the transform operates and performs. As an example, in one embodiment of the present invention, a two-second window averaged for periods of about one minute, or even longer, is used to convert the time-domain signal.

One novel realization reached by the present inventor is that the frequency domain signals are visually informative when arranged in a log-log format, in step 206. In particular, the y-axis represents the power, or power spectral density (PSD), of a frequency in the signal and the x-axis represent the frequency. Both axes, though, are scaled logarithmically. What results is a visual display that reveals that the resulting frequency-domain data can generally be split into multiple regions—a first region from about 0 to about 10 or 20 Hz, a second region representing the frequencies above the first (to about 40 Hz); and a third region typically associated with EMG signals between about 40 Hz and 130 Hz. The first range can extend further as well, especially when the patient is in a state of awareness. These regions will be conveniently referred to as a low frequency segment, a high frequency segment, and an EMG segment. Those labels are used as a way of convenience and of comparison to each other and are not intended to limit the segments in any way to a particular range of frequencies.

Once the frequency-domain data points are arranged in this log-log format, a best-fit line is calculated in steps 208. In particular, one or more best fit lines are calculated for each segment. One of the easiest best-fit approaches is to use a least-squares approach but one of ordinary skill will recognize that there are numerous other data regression schemes that may be used to approximate a line while minimizing error. In one example, the best fit lines were accomplished using an iterative least-squares approach where the slope and y-intercept of a line providing the minimum mean square between the log of the spectral magnitude and that line were obtained. Also, one of ordinary skill will recognize that optional methods of fitting the data may be accomplished during the least-squares fit as well. For example, points that are statistical outliers can be discarded if their error size suggests that they should not be used when fitting the data to the best-fit line. The best-fit line can then be recalculated with the outliers ignored As mentioned, different regression methods other the least-squares may be used to calculate the best fit lines and furthermore, one regression method may be used for the high frequency line and a different regression method used for the low frequency line and yet a third regression method may be used for the best fit line of the EMG segment.

The determination of when the best fit lines are complete can be accomplished in a number of different ways. The determination can be based on an event in the EEG or EMG signal itself. For example, the EEG signal may exhibit an alpha-peak at a certain frequency and that value is used for the endpoints of the two best-fit lines of the high and low frequency segments. For example, the first best-fit line is calculated from the lowest frequency to the alpha-peak frequency and the second best-fit line is calculated from the alpha-peak frequency to the highest frequency. The alpha-peak frequency, itself, can be selected in different ways such as at the beginning of the peak, a center frequency, or at the end of the peak. Alternatively, the decision to stop the least-squares fitting can be determined on the fly as the best-fit lines are being calculated. For example, an analysis can be made to determine when a similar frequency is reached from both directions at which both the first best-fit line and the second best-fit line start deviating significantly (e.g., some percentage, such as, for example 3% to 8%) from the previously calculated best-fit line. This frequency, then, is the dividing point between the two best-fit line segments.

Once the best-fit lines are determined, then the slope of each line can be calculated and the intersection point as well with the neighbor segment (see step 210). Of particular interest is the frequency at the intersection point. Based on the relative slopes of the best-fit lines and the frequency of the intersection points, an indication is generated, in step 212, that relates to the state of anesthesia, or the state of awareness, of the patient.

FIG. 2B depicts a log-log display of an EEG signal 230 that is represented with two best fit lines 232 and 236. The peak 234 appears to be present but a clinician can benefit from additional indicators regarding the state of the patient. Thus, in accordance with the principles of the present invention, the region to the right of the intersection point is broken into different sections 238, 240, and 242 that are graphically displayed to the clinician. While more or fewer sections could be utilized, three sections are beneficial because it allows a comfortable granularity for quick decision making. The sections 238, 240, and 242 represent different angular areas with respect to the intersection point 234 and the slope of the higher frequency line(s) 236. The slope of the line depends, of course, on the scale of the x and y-axis of the graph. Generally speaking, however, a line 236 with a small steep slope (e.g., more negative than −40 dB/decade) would be located in region 238; a line 236 with a relatively shallow slope (e.g., more shallow than about −30 dB/decade) would be located within the top region 242, and a line 236 in-between these approximate values would be located in the middle region 240.

Using the additional information provided by the three sections, a clinician can confirm that peak, or spindle, activity is indicative of the state of the patient. For example, when the line 236 is in the lower region 238 and there is an apparent alpha-peak (as shown in FIG. 2B), then these two pieces of evidence allow the clinician to be more certain that the patient is properly anesthetized. FIG. 2C depicts a different situation. The EEG signal 260 is depicted by a first line 262, an intersection point 264, and a second line 266. Although there may be a peak in this display, the location of the higher frequency line(s) 266 is within the middle region 240 and near the top region 242 instead of near the lower region 238. Given this display, the clinician can become concerned that the patient is becoming more awake and adjust anesthesia accordingly.

One current monitor that tracks anesthetic effects on the brain, Aspect's Bispectral Index monitor (BIS) is less than ideal. BIS is an index value that at best correlates with a probability of awareness. BIS was empirically developed based on a theory of anesthetic action as it relates to electroencephalography (EEG) analysis which has never been proven. BIS is composed of 3 sub-parameters. One is suppression ratio. Another is the beta ratio which is the log of the ratio of power in 30-47 Hz to 11-20 Hz. The third sub-parameter is a Bispectral parameter called SynchFastSlow. The visual technique of displaying the EEG signal as described above can be used as a sole indicator of patient awareness or could also be used along with another indicator, such as BIS, as a way to verify that other indicator.

The starting and ending values of each of the three regions as well as their sizes relative to one another can vary according to patient type. Thus, the age and other factors about a patient can be used to customize the location and size of the three regions. However, the intersection of the two best-fit lines is the most beneficial place from which to define the different angular sections because the intersection point accounts for variance in both amplitude and frequency of features of the EEG spectrum. While the intersection point remains in generally the same neighborhood on the graph, this intersection point can move slightly based on characteristics of the EEG spectrum. Thus, the intersection point can be represented by an average of the instantaneous values of the intersection point over a predetermined time window. For example, a time window that varies from about two seconds to about 30 seconds could be used to calculate a moving average intersection point.

It is possible to achieve similar, although inferior results, using the EEG spectrum itself without the benefit of calculating the best-fit lines and their intersection point. In the EEG spectrum there is a "spectral edge" that can be identified where the general trend of the higher frequencies (e.g., about 10 Hz) drops dramatically lower than the general trend of the lower frequencies. This "spectral edge" value can be used as the originating point of the angular sections of the template discussed above. One formal definition of "spectral edge" is the frequency below which 95% of the power in the power spectrum resides; however, embodiments of the present invention contemplate that a beneficial result can be obtained by varying the spectral edge frequency from about +1-3% from the typical 95% threshold. In the techniques described above, a best-fit line was calculated for the higher frequencies. As one alternative, instead of calculating a best fit line for the higher frequencies, the EEG spectrum itself is considered when determining which of the angular sections it occupies. Thus, a template can be used with just the EEG spectrum to provide an indication or a verification of the awareness of a patient.

While the above techniques have been discussed solely within the context of a log-log graph, similar techniques would also work with a log-linear graph but the lines would be curved. Additionally, when more than two best-fit lines are calculated there is more than a single intersection point that can be useful in defining a template. Thus, at each of the other intersection points a respective set of additional angular sections can be defined for the template. It is contemplated that each intersection point would have its own set of three angular sections defined similar to the techniques described above; however, defining only two angular sections for the additional intersection points is contemplated as well. As a result, the clinician may be presented with a display in which a certain portion of the EEG power spectrum is in a "green" portion of the template for one range of frequencies but in a "yellow" or "red" portion of the template for a different range of frequencies. Based on this type of multi-part template the clinician can draw further conclusions about the state of awareness of the patient.

The description above specifically used a plurality of angular sections as the template by which to compare an EEG signal or the best fit lines. However, this is only one specific example of a template that can be used. In the more general case, a number of templates can be defined from empirical evidence that describe the EEG signals of a history of different patients. As a current patient's EEG signal is acquired, and possibly filtered or transformed, it can be compared with the database of possible templates. The current EEG signals can be mathematically compared with the templates to determine which template is most similar to the current signal. Based on that determination and prior knowledge about the matching template, an indication can be provided about the state of the patient's awareness. In other words, if a template is known to show a person starting to become more awake and the current EEG signals match that template, then the clinician can receive a warning indication that the patient may be awakening.

Figure 3:
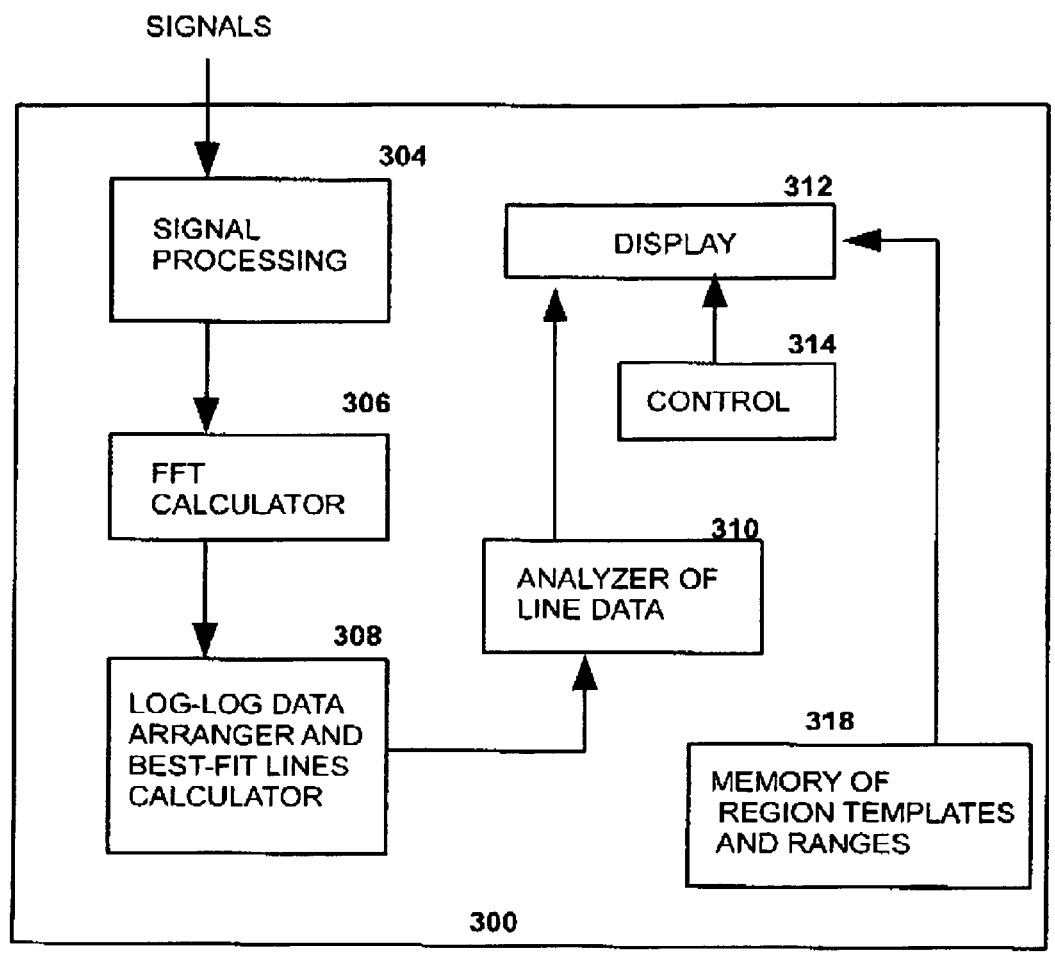
FIG. 3 shows an apparatus on which the flowchart of FIG. 2A may be performed in accordance with the principles of the present invention.

FIG. 3 illustrates an automated platform on which the algorithm described above may be implemented. In practice, the device 300 would be used during surgery to monitor the anesthesia state of the patient to allow an anesthesiologist to modify the delivery of an anesthetic agent as appropriate. The device 300 is shown in functional block form in FIG. 3 because the different functional blocks may be implemented in a variety of ways without departing from the scope of the present invention. For example, a programmable computer with a typical microprocessor may implement a variety of the functions in software programs that are stored on an accessible media and executed during operation. Alternatively, some of the functions may be implemented using specialized hardware including DSP chips and microcontrollers. One of ordinary skill will recognize that various combinations of hardware and software may be utilized to accomplish the functions of the blocks shown in FIG. 3.

The EEG and EMG signals 302 are received and then filtered and converted by a signal processor 304. That signal can then be transformed into the frequency domain by a fast Fourier transformer 306. The power spectrum of the frequency domain signal can then be calculated in a log-log arrangement so that an interpolator 308 can calculate multiple best-fit lines for the spectrum. An analyzer 310 analyzes the best fit lines to determine their respective slopes and the frequency at which they intersect.

Based on the calculations of the analyzer 310 a display 312 provides an indication of the anesthesia state of the patient. The display 312 may be multifaceted to provide the viewer of the display with different information. Two particularly relevant pieces of data are a) the difference between the slopes of the best-fit lines and b) the frequency at which the lines intersect. Thus, these values may be displayed as raw numeric information. A graphical display may be included which graphs these values in a historical fashion so that the viewer of the display can see how the values have been changing in some preset time period. For example, the display could show the values over a window depicting the last 5 minutes. A control 314 for the display 312 can be used to allow the viewer to change between different formats of output as desired. The display 312 can also be configured to display the best-fit lines in near real-time with (or without) the additional values discussed above.

There is a memory 318 that stores the values for different region templates based on patient parameters (e.g., sex, age, drug use, head injury history, etc.). Using these patient factors, an appropriate template is also displayed along with the best fit lines and/or the raw EEG signal in order to give the clinician additional confirmation of suspected spindle activity. The display of the template having these three (or more) angular sections can be accomplished in a variety of ways. For example, the colors of the regions (e.g., red, yellow, green) can be used to provide additional visual clues regarding the patient's condition. For example, if the best-fit line is in the lower region, then the background of that section of the display can be green. If the best-fit line is in other angular sections of the template, then the background of those sections can be red or yellow. In this way, the clinician can be alerted by simply seeing which color is being displayed in the higher frequency region of the display.

Also, (not shown) the device 300 may included a storage function that records various signals and calculations during the duration of the surgery.

Other aspects of the present invention include filtered time domain EEG. (display and use for analysis). "Raw EEG" displays are filtered but over a broad range such as >1 Hz and <100 Hz and a 60 Hz notch filter. However, a more narrow filtered time domain allows the clinician to see the oscillation that creates the alpha peak without the interference of either low frequency baseline changes or high frequency EMG noise. It also enables the clinician to verify the interpretation of the spectrogram.

For example, one filtered signal could include a display in the operating room of narrow range filtered time domain signal such as 7-14 Hz to show the spindle oscillation. A declining amplitude of this oscillation indicates either light or deep anesthesia.

Other examples include multiple filtered ranges to show changes in other oscillations. This can help with interpreting changes in the spindle oscillation.

Additionally, the filter widths can be adjusted to capture the activity of a changing peak width and center frequency (and the changing values over time of the width height and center frequency of the peak controlling the filter.)

Essentially, the filtering of the signals can accomplish filtering out of the EMG noise. The spectral data itself of the signal can be used to determine what type of filtering will occur. In particular, the location and amplitude of one or more of the peaks (and their shape) can be used to determine how filtering takes place.

Figure 4:
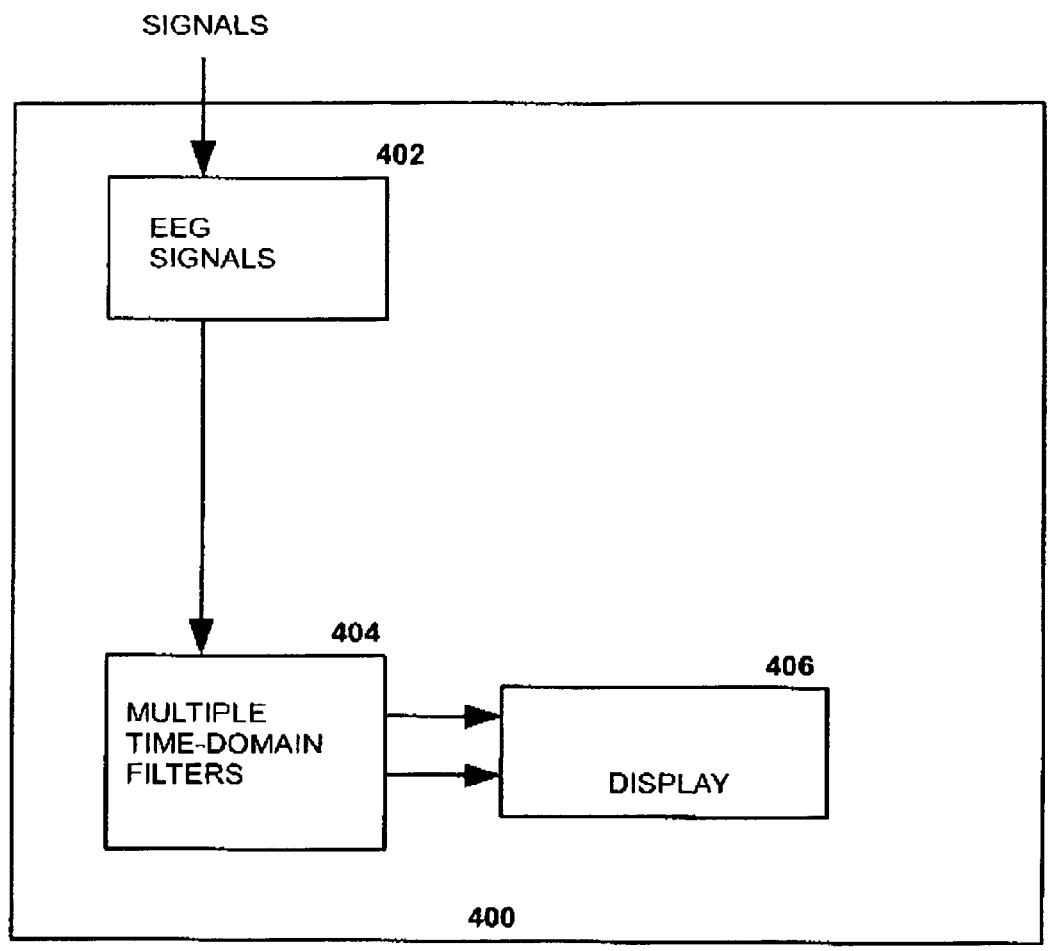
FIG. 4 shows an apparatus which may operate in accordance with the principles of the present invention.

FIG. 4 illustrates an automated platform on which the filtering functions described above may be implemented. In practice, the device 400 would be used during surgery to monitor the anesthesia state of the patient to allow an anesthesiologist to modify the delivery of an anesthetic agent as appropriate. The device 400 is shown in functional block form in FIG. 4 because the different functional blocks may be implemented in a variety of ways without departing from the scope of the present invention. For example, a programmable computer with a typical microprocessor may implement a variety of the functions in software programs that are stored on an accessible media and executed during operation. Alternatively, some of the functions may be implemented using specialized hardware including DSP chips and microcontrollers. One of ordinary skill will recognize that various combinations of hardware and software may be utilized to accomplish the functions of the blocks shown in FIG. 4.

The EEG signals (analog) are received and initially filtered in a receiver 402. For example, the raw signals can initially be filtered such that signals from about 1 Hz to about 100 Hz are analyzed. Other ranges of frequency filtering can be used as well without departing from the scope of the present invention. Next, this signal can be fed to multiple time-domain filters 404. For example, there can be a filter that passes only the alpha waves, another filter that passes only the beta waves, another filter that passes on the gamma waves, and another filter that passes only the delta waves. The different filtered waveforms can then be displayed visually on a display 406.

Frequency domain methods require 30 to 60 seconds to assess the EEG spectrum. The time domain can give instant information that the situation has changed. Currently utilized time domain methodology is a single unfiltered "raw" EEG signal. Multiple neurophysiologic processes can occur simultaneously making the "raw" signal difficult to interpret. Multiple filtered displays can help to identify the different processes and create an indication of the neurophysiologic state.

One such process is the spindle oscillation. Verification that this process is occurring can indicate that the patient is in an unconscious state. To verify the spindle it is useful to have displays that are filtered to exclude activity outside of the spindle range which is 7-14 Hz. One display is at a sufficient speed to identify oscillations that have a wavelength of about 100 msec. One inch per second is a good example. Since the spindle oscillations occur in packets with gaps in between packets (not a continuous oscillation) it is useful to have a second window at a speed that is about one inch per ten seconds. A third display that shows the trend for long periods of time is also useful.

Another process worth monitoring with a filtered time domain display is the gamma band which is above 25 Hz and extending to 40 or 50 Hz. Increased activity in this frequency range could indicate that the patient is becoming aware. (Gamma could also be EMG.) Arranging gamma band windows at the same speed as the alpha band displays is useful to create an indication of the neurophysiologic state. Having the different frequency bands arranged one frequency directly above the other helps to make the assessment. Packets of spindles do not begin and end at the same time as packets of gamma band activity. Burst suppression is a neurophysiologic state where packets of oscillations begin at the same moment at multiple frequency bands. Burst suppression is usually identified by the periods of electrical silence (suppression). However, there can be continuous bursting with few or no periods of electrical silence. When that occurs the multiple filtered band displays are useful to identify bursting from spindling.

The filtering and display of the different time domain bands utilize different display window sizes (in the time dimension) and different frequency bands. For example, the display of the alpha wave signals in one window may show a 2 to 4 second snapshot of the wave while another display shows about a 30 second snapshot of the same wave. In this way, the clinician can see the current activity of a particular frequency band as well as the recent trend of that frequency band. A third window can be used to display the historical trend of a particular frequency band since a procedure was started.

In at least one embodiment, the different frequency bands are shown in separate windows while in other embodiments, the signals of the different frequency bands can be superimposed within the same window.

Figure 5:
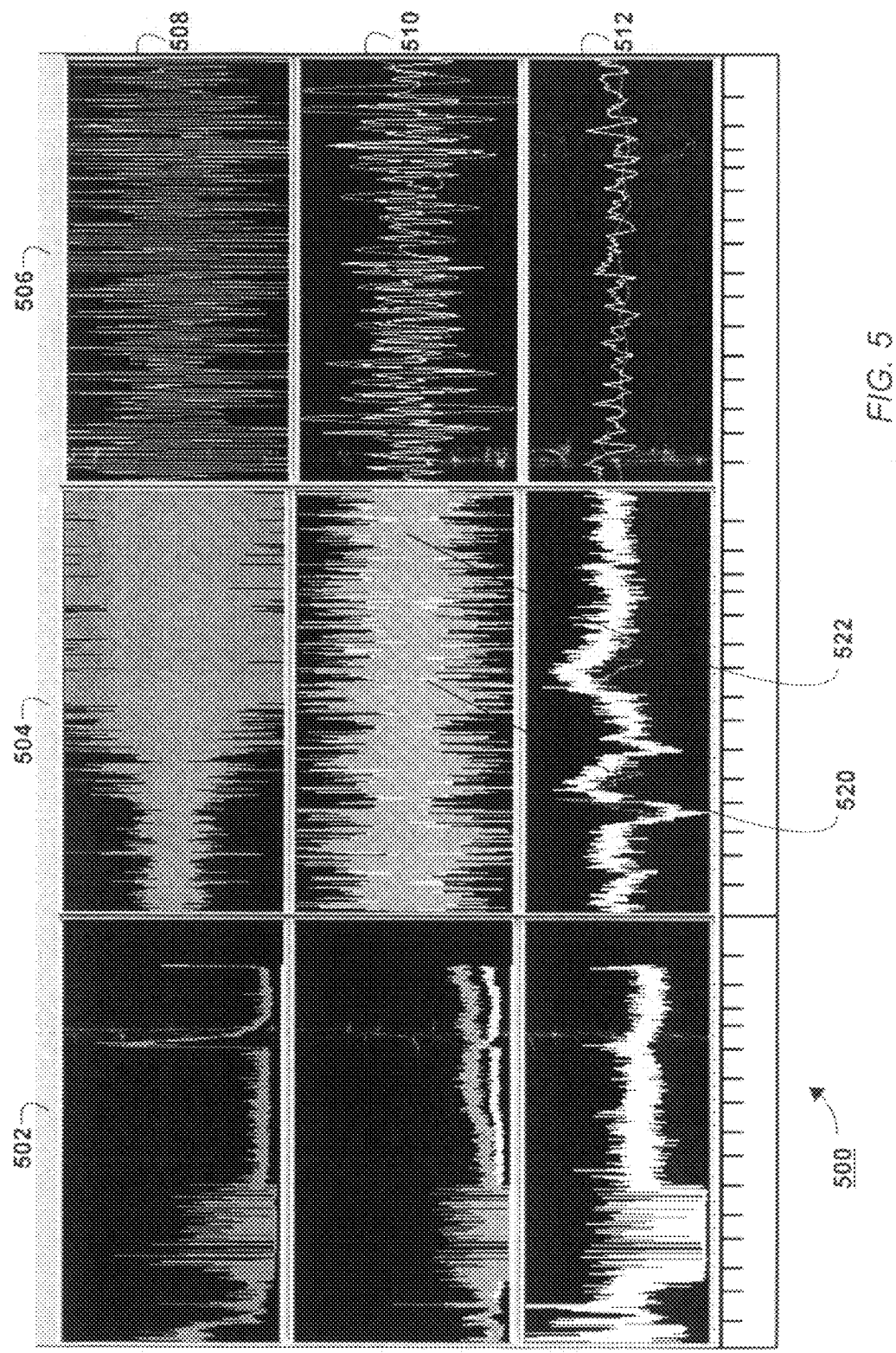
FIG. 5 illustrates an exemplary display in accordance with the principles of the present invention.

FIG. 5 illustrates an exemplary display in accordance with the principles of the present invention. The display 500 is an example only and is not intended to limit the present invention to a 3×3 grid of windows. In general, the display 500 shows that multiple frequency bands of EEG time domain signals are displayed in windows having different time scales. In addition, the different waveforms can be shown in different colors so as to visually distinguish each signal from another.

In FIG. 5, there are three different time scale windows represented by the columns 502, 504 and 506. The physical size of the apparatus which presents the display 500 plays a factor but typically the time scales for the different windows are chosen to provide useful, visual information to a clinician. For example, alpha waves range from about 7 Hz to about 14 Hz, so a two second window (column 506) displays the individual cycles of the alpha waves. However, a 30 second window of about the same size (as depicted in column 504) will show packets of alpha wave peaks rather than the individual cycles themselves. A third time value window 502 can show a long period of time so that the trend or RMS power of a signal can be evaluated.

The rows 508, 510, 512 of the display 500 represent different frequency bands. For example, the top row 508 can show delta or theta waves or might even show the raw EEG signal. The second row 510 can show the alpha wave band and the bottom row 512 can show another frequency band such as the gamma waves. Thus, each row can represent a different frequency band of the EEG signal. Of course one of ordinary skill will appreciate that the positions of the different bands can vary; for example, the bottom row 512 can be used to display the raw EEG signal and the top row 508 could be used to display the gamma band or some other frequency band. In addition, it is beneficial to superimpose different frequency bands over one another as well. For example, the middle window shows two signals 520, 522 having different colors. If for example, the white signal 522 is the beta wave band and the gray signal 520 is the alpha wave band, then the amount of the different colors that are visible will visually alert a clinician when the beta activity is increasing and the alpha activity is decreasing. Thus, there is an indication to the clinician that the patient may be awakening or that the there is little fear of the patient awakening.

The previous description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with each claim's language, wherein reference to an element in the singular is not intended to mean "one and only one" unless specifically so stated, but rather "one or more." All structural and functional equivalents to the elements of the various embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for."

What is claimed is:

1. A method for providing an indication of a state of awareness for a patient, comprising the steps of:
    displaying data of an EEG power spectrum to provide a power versus frequency graph;
    determining, using a processor, a frequency value that separates a lower frequency region from a higher frequency region of the EEG power spectrum;
    generating, using the processor, a template, wherein the template has a plurality of contiguous angular sections originating at the frequency value; and
    providing, using the processor, an indicator of the state of awareness of the patient based on a position of at least a portion of the higher frequency region coinciding with one of the plurality of contiguous angular sections.

2. The method of claim 1, wherein the plurality of contiguous angular sections has three angular sections.

3. The method of claim 1, wherein data of the EEG power spectrum is displayed in a log-log arrangement.

4. The method of claim 3, further comprising:
    calculating a first best-fit line for a lower frequency region of the EEG power spectrum; and
    calculating at least a second best-fit line for a higher frequency region of the EEG power spectrum.

5. The method of claim 4, wherein the frequency value is the intersection point of the first and second best-fit lines.

6. The method of claim 5, further comprising:
    providing the indicator of the state of awareness of the patient based on a position of the second best-fit line coinciding with one of the plurality of contiguous angular sections.

7. The method of claim 4, further comprising:
    displaying the first and second best-fit lines.

8. The method of claim 4, wherein the plurality of contiguous angular sections includes:
    a first angular section which represents a region having a first slope steeper than about −40 dB/decade;
    a second angular section which represents a region having a second slope more shallow than about −30 dB/decade; and
    a third angular section which represents a region between the first and second angular sections.

9. The method of claim 8, wherein each of the plurality of contiguous angular sections has a respective associated color.

10. The method of claim 9, further comprising:
    determining in which particular one of the plurality of contiguous angular sections the second best-fit line is located; and
    wherein providing the indicator includes displaying the respective color associated with the particular one of the plurality of contiguous angular sections.

11. The method of claim 4, further comprising:
    determining the intersection point of the first best-fit line and the second best-fit lines.

12. The method of claim 1, wherein data of the EEG power spectrum is displayed in a log-linear arrangement.

13. The method of claim 1, wherein the plurality of contiguous angular sections includes:
    a first angular section which represents a region having a first slope steeper than about −40 dB/decade;
    a second angular section which represents a region having a second slope more shallow than about −30 dB/decade; and
    a third angular section which represents a region between the first and second angular sections.

14. The method of claim 1, wherein the indicator includes displaying at least a portion of the particular one of the contiguous angular sections of the template generated.

15. The method of claim 1, further comprising:
    selecting the template from among a plurality of different templates based on a characteristic of the patient.

16. An apparatus for providing an indication of a state of awareness for a patient, comprising the steps of:
    a receiver configured to acquire an EEG signal;
    a visual display screen coupled with the receiver and configured to display data of an EEG power spectrum to provide a power versus frequency graph;
    a calculator coupled with the receiver and configured to determine a frequency value that separates a lower frequency region from a higher frequency region of the EEG power spectrum;
    the calculator further configured to generate a template, wherein the template has a plurality of contiguous angular sections originating at the frequency value; and
    an indicator coupled with the calculator configured to provide an indicator of the state of awareness of the patient based on a position of at least a portion of the higher frequency region coinciding with one of the plurality of contiguous angular sections.

17. The apparatus of claim 16, wherein the visual display screen is configured to display the EEG power spectrum in a log-log arrangement.

18. The apparatus of claim 17, wherein the calculator is further configured to:
    calculate a first best-fit line for a lower frequency region of the EEG power spectrum;
    calculate at least a second best-fit line for a higher frequency region of the EEG power spectrum; and
    calculate the an intersection point of the first and second best fit lines, wherein the intersection point is the frequency value that separates a lower frequency region from a higher frequency region of the EEG power spectrum.

19. The apparatus of claim 18, wherein the plurality of contiguous angular sections includes:
    a first angular section which represents a region having a first slope steeper than about −40 dB/decade;
    a second angular section which represents a region having a second slope more shallow than about −30 dB/decade; and
    a third angular section which represents a region between the first and second angular sections.

20. The apparatus of claim 19, wherein the indicator is based on a position of the second best-fit line coinciding with one of the plurality of contiguous angular sections.

* * * * *